(12) United States Patent
Wada et al.

(10) Patent No.: US 8,043,564 B2
(45) Date of Patent: Oct. 25, 2011

(54) COPOLYMER, AND ADSORBENT OR CONCENTRATING MEDIUM AND NEEDLE FOR SOLID PHASE MICROEXTRACTION PREPARED USING THE COPOLYMER

(75) Inventors: Hiroo Wada, Kyoto (JP); Kenzo Kotera, Kyoto (JP); Hisashi Matsuura, Kyoto (JP); Kiyokatsu Jinno, Toyohashi (JP); Yoshihiro Saito, Toyohashi (JP)

(73) Assignee: Shinwa Chemical Industries, Ltd., Kyoto-shi (JP)

( * ) Notice: Subject to any disclaimer, the term of this patent is extended or adjusted under 35 U.S.C. 154(b) by 1849 days.

(21) Appl. No.: 10/682,903

(22) Filed: Oct. 14, 2003

(65) Prior Publication Data

US 2004/0091400 A1    May 13, 2004

(30) Foreign Application Priority Data

Oct. 16, 2002 (JP) .................. 2002-302014

(51) Int. Cl.
*B01D 15/00* (2006.01)
*G01N 30/96* (2006.01)
*C02F 1/42* (2006.01)
(52) U.S. Cl. ............ 422/88; 422/69; 436/178; 210/660
(58) Field of Classification Search .............. 422/69, 422/88; 210/660; 436/178
See application file for complete search history.

(56) References Cited

U.S. PATENT DOCUMENTS

| | | | |
|---|---|---|---|
| 3,431,226 A | | 3/1969 | Warson et al. |
| 3,831,555 A | * | 8/1974 | Srinivas ............ 118/506 |
| 4,631,177 A | * | 12/1986 | Yotsuyanagi et al. ........ 423/112 |
| 4,732,046 A | * | 3/1988 | Lawrence et al. .......... 73/864.21 |
| 5,223,226 A | * | 6/1993 | Wittmer et al. ............ 422/100 |
| 5,422,405 A | * | 6/1995 | Dairoku et al. ............ 525/384 |
| 5,496,473 A | * | 3/1996 | Chow ..................... 210/635 |
| 5,705,553 A | | 1/1998 | Kuropka |

(Continued)

FOREIGN PATENT DOCUMENTS

EP    0 068 509    1/1983

(Continued)

OTHER PUBLICATIONS

Lai et al., Surface Plasmon Resonance Sensors Using Molecularly Imprinted Polymers for Sorbent Assay of Theophylline, Caffeine, and Xanthine, Canadian Journal of Chemistry, vol. 76, Issue 3, p. 265-273, Mar. 1998.*

(Continued)

*Primary Examiner* — In Suk Bullock
*Assistant Examiner* — Paul Hyun
(74) *Attorney, Agent, or Firm* — Oblon, Spivak, McClelland, Maier & Neustadt, L.L.P.

(57) ABSTRACT

Described is a copolymer of methacrylic acid and ethylene glycol dimethacrylate which does not have any specificity to general organic solvents, can thus adsorb wide variety of the organic solvents, shows almost no desorption-adsorption hysteresis and therefore, is excellent in desorption characteristics. Also described is a method for the preparation of the copolymer; an adsorbent or a concentrating medium comprising the copolymer; a loop used in an injector for chromatography which is packed with the adsorbent or concentrating medium; a needle for solid-phase microextraction (SPME) which is packed with the adsorbent or concentrating medium; a kit for the preparation of a sample comprising the needle for SPME; a method for concentrating a sample; and a method for analyzing an analyte present in a sample.

18 Claims, 3 Drawing Sheets

U.S. PATENT DOCUMENTS

| | | | |
|---|---|---|---|
| 6,054,047 A * | 4/2000 | Hindsgaul et al. | 210/198.2 |
| 6,354,135 B1 * | 3/2002 | McGee et al. | 73/23.34 |
| 6,780,314 B2 * | 8/2004 | Jinno et al. | 210/198.2 |
| 2003/0166798 A1 * | 9/2003 | Sellergren et al. | 525/540 |
| 2004/0009872 A1 * | 1/2004 | Cohen et al. | 502/402 |

FOREIGN PATENT DOCUMENTS

| | | |
|---|---|---|
| EP | 0 551 699 | 7/1993 |
| EP | 0 686 650 | 12/1995 |
| JP | 58-17844 | 2/1983 |
| JP | 63-68615 | 3/1988 |
| JP | 5-178912 | 7/1993 |
| JP | 11-83826 | 3/1999 |
| WO | WO 02/16442 | 2/2002 |

OTHER PUBLICATIONS

Derwent Abstracts, AN 1983-15645, XP-002264977, JP 58-000244, Jan. 5, 1983.
Derwent Abstracts, AN 1983-745256, XP-002264978, SU 966092, Oct. 15, 1982.
Patent Abstracts of Japan, JP 05-194617, Aug. 3, 1993.
Patent Abstracts of Japan, JP 05-093004, Apr. 16, 1993.

* cited by examiner

POLYMER   FUSED SILICA   TWO-PACK TYPE ADHESIVE

FIG.3

NASLON FILTER   COPOLYMER   LOOP (MADE OF STAINLESS STEEL)

COPOLYMER, AND ADSORBENT OR CONCENTRATING MEDIUM AND NEEDLE FOR SOLID PHASE MICROEXTRACTION PREPARED USING THE COPOLYMER

BACKGROUND OF THE INVENTION

The present invention relates to a novel copolymer and applications thereof and more specifically the present invention pertains to a copolymer of methacrylic acid with ethylene glycol dimethacrylate; a method for the preparation thereof; an adsorbent or a concentrating medium containing the same; a loop of an injector for chromatography packed with the adsorbent or concentrating medium; a needle for solid phase micro-extraction (SPME) packed with the adsorbent or concentrating medium; a kit containing the needle and used for the preparation of a sample for analysis; and a method for concentrating a sample and a method for analyzing an analyte present in the sample, which make use of the kit.

The solid phase microextraction (hereunder referred to as "SPME" or "solid phase extraction") is a most powerful or effective tool for the preliminary concentration of a sample, which is inspected for the presence of an organic compound to be analyzed, such as an aqueous sample analyzed according to the gas chromatography (GC) technique. The SPME technique may simply be handled and requires the use of a small amount of a solvent consumed, as compared with the conventional solvent extraction technique and therefore, there have been presented or proposed a large number of applications of the SPME/GC technique. When dipping an SPME fused silica rod in the sample solution, the analyte is extracted into the polymer film on the surface of the silica rod. Then the fused silica rod is introduced into the sample-injection port of a gas chromatograph and a heat is then applied thereto so that the analyte molecules undergo desorption by the action of the heat. In contrast with the foregoing succeeded example, there have been known only a small number of reports concerning the combination of the SPME technique with the liquid chromatography (LC) technique or the electrophoretic separation technique for the analysis of a non-volatile compound. This is because, the mechanism of the on-line interface is complicated and the operations for desorption are quite difficult.

Recently, there has been developed another SPME technique or an in-tube SPME technique in which the LC separation device is directly connected to the SPME device without using any interface. In this method, the extraction medium used is an open tubular GC hollow capillary column. If a sample solution is passed through the column using a microflow pump, an analyte present in the aqueous sample solution is extracted into a polymer film applied onto the inner wall of the hollow capillary. A small amount of an organic solvent can likewise be passed through the hollow capillary to thus desorb the analyte thus extracted. This method does not require the use of any desorption device for feeding the extracted solute into the separation device and therefore, any process requiring difficult operations can be eliminated and the amount of the organic solvent required for the desorption can be reduced to a level as low as possible.

The inventors of this invention have already tried to adopt a wire-in-tube structure as a hollow capillary for extraction used in the analysis of a tricyclic antidepressant present in the human urine. In this wire-in-tube structure, the inner volume of the hollow capillary for extraction can substantially be reduced by the insertion of a stainless wire into the hollow capillary, while maintaining the surface area, which comes in contact with a sample solution. Such a construction would permit the further improvement of the concentration effect as compared with that achieved by the conventional in-tube SPME technique. Moreover, this fact suggests that the on-line wire-in-tube SPME/LC device would enable the high-speed analysis of a variety of organic compounds present in biological and environmental sample matrices.

On the other hand, the analysis of phthalic acid esters present in aqueous sample matrices in low concentrations have been considered as one of most important problems to be solved because of the estrogen actions of the compounds. There have widely been investigated techniques for the quantitative analysis of phthalic acid esters as internal secretion-disturbing substances and for elucidating the functions thereof, but there has still been desired for the development of an effective and rapid extraction-concentration technique, which never requires the use of a large amount of a solvent, in the practical analysis of environmental aqueous samples.

Further, there has been proposed a technique, which makes use of polymers derived from divinyl benzene as a medium used in the absorption-desorption of the foregoing samples to be analyzed. However, only specific samples are adsorbed on such polymers and, in particular, these polymers suffer from various problems. For instance, they cannot adsorb any alcohol, it is difficult to use them since the particle size thereof is too small and they are quite susceptible to water vapor. For this reason, there has been desired for the development of an absorption-desorption medium usable for various purposes.

SUMMARY OF THE INVENTION

Accordingly, it is a first object of the present invention to provide a novel copolymer useful as an absorption-desorption medium.

It is a second object of the present invention to provide a method for the preparation of the foregoing novel copolymer.

It is a third object of the present invention to provide an adsorbent or a concentrating medium used for adsorbing and/or concentrating a sample.

It is a fourth object of the present invention to provide a loop of an injector for chromatography.

It is a fifth object of the present invention to provide a needle for solid phase microextraction (SPME).

It is a sixth object of the present invention to provide a kit for the preparation of a sample to be analyzed.

It is a seventh object of the present invention to provide a method for adsorbing and concentrating an analyte present in a sample to be analyzed.

It is an eighth object of the present invention to provide a method for analyzing an analyte present in a sample to be analyzed.

According to a first aspect of the present invention, there is provided a copolymer of methacrylic acid and ethylene glycol dimethacrylate.

According to a second aspect of the present invention, there is provided a method for preparing a copolymer of methacrylic acid and ethylene glycol dimethacrylate comprising the step of polymerizing methacrylic acid and ethylene glycol dimethacrylate in a polyvinyl alcohol aqueous solution.

According to a third aspect of the present invention, there is provided an adsorbent or a concentrating medium used for adsorbing and/or concentrating a sample, which contains the foregoing copolymer.

According to a fourth aspect of the present invention, there is provided a loop of an injector for chromatography, which is packed with the foregoing adsorbent or concentrating medium.

According to a fifth aspect of the present invention, there is provided a needle for solid phase microextraction (SPME), which is packed with the foregoing adsorbent or concentrating medium.

According to a sixth aspect of the present invention, there is provided a kit for the preparation of a sample to be analyzed, which comprises the foregoing needle for SPME, a large volume syringe and a small volume syringe.

According to a seventh aspect of the present invention, there is provided a method for concentrating a sample comprising the step of aspirating a sample into the large volume syringe of the kit for the preparation of a sample to be analyzed to adsorb an analyte present in the sample on the adsorbent or concentrating medium within the needle for SPME and to thus concentrate the analyte present in a sample.

According to an eighth aspect of the present invention, there is provided a method for analyzing an analyte present in a sample to be analyzed characterized by comprising the steps of aspirating a sample into the large volume syringe of the kit for the preparation of a sample to adsorb an analyte present in the sample on the adsorbent or concentrating medium within the needle for SPME, substituting the small volume syringe for the large volume syringe, inserting the needle for SPME into a sample-injection port of a chromatograph, passing an elution medium fed from the small volume syringe through the needle to thus elute the analyte adsorbed on the adsorbent or concentrating medium and injecting the eluted analyte into the chromatograph through the sample-injection port thereof to thus carry out the chromatography analysis.

BRIEF DESCRIPTION OF THE INVENTION

DESCRIPTION OF THE PREFERRED EMBODIMENTS

The present invention will hereunder be described in more detail with reference to the following preferred embodiments of the present invention optionally described while referring to the accompanying drawings.

First, the novel copolymer of the present invention will be detailed below.

The copolymer of the present invention is produced from methacrylic acid and ethylene glycol dimethacrylate. The molar ratio of methacrylic acid and ethylene glycol dimethacrylate in the copolymer preferably ranges from 1:1 to 10 and more preferably 1:4 to 6.

The copolymer of the present invention may comprise monomers other than the foregoing ones as copolymer components. Examples of such other monomers usable as copolymer components are vinyl pyridine, methyl methacrylate, trimethylolpropane trimethacrylate, pentaerythritol tetramethacrylate and glycidyl methacrylate. In this connection, the amount of such other monomers is suitably not more than 50% by mass on the basis of the total mass of the copolymer.

The copolymer according to the present invention can easily be prepared by copolymerizing methacrylic acid, ethylene glycol dimethacrylate and a third monomer as an optional component.

The polymerization can be carried out by, for instance, dissolving a water-soluble metal salt such as a water-soluble alkali metal salt (e.g., sodium chloride) in an aqueous solution containing 1.0 to 5.0% by mass of polyvinyl alcohol having a weight average molecular weight of about 22,000-88,000, polyvinyl pyrrolidone having a weight average molecular weight of about 40,000-360,000 or the like (which serves as a dispersing agent) in a concentration ranging from 1.0 to 3.0% by mass; adding desired amounts of methacrylic acid and ethylene glycol dimethacrylate, 0.5 to 2.0% by mass of a polymerization initiator (such as azoisobutyronitrile, benzoyl peroxide, hydrogen peroxide) and 0 to 200% by mass of a swelling agent (such as di-n-butyl phthalate, toluene, isooctane, liquid paraffin); and then reacting these components at a temperature ranging from 50 to 100° C., preferably 70 to 90° C. for 10 minutes to 5 hours and preferably 30 minutes to 2 hours. Since the copolymer produced after the completion of the reaction is precipitated, the precipitates are separated, washed with water, preferably hot water, then several times with acetone, several times with water and finally several times with acetone and subsequently drying the precipitates to thus obtain the desired copolymer. The swelling agent does not take part in the reaction, is removed through the washing with acetone and thus forms fine pores within the copolymer thus produced. Accordingly, the volume of fine pores present in the copolymer can be controlled by appropriately adjusting (increasing or decreasing) the amount of the swelling agent to be added to the reaction system. The copolymer thus produced is in the form of beads having a particle size ranging from about 20 to about 100 μm and therefore, the copolymer is not extremely fine unlike the polymer conventionally used as a medium.

The water-soluble metal salt may serve to inhibit any dissolution of monomers in water and to improve the reaction efficiency.

The copolymer of the present invention can be used as an adsorbent or a concentrating medium for the adsorption and/or concentration of samples to be analyzed or the like without any post-treatment, independently or in combination with other polymer components such as polymers derived from divinyl benzene and other components, for instance, adsorbent such as silica gel and activated carbon.

In the case where the copolymer of the present invention is used as an adsorbent or a concentrating medium, it is quite convenient to use the copolymer as a packing material for a needle for SPME.

Such a needle is desirably one produced from a metal such as stainless steel. The dimension thereof is not particularly restricted, but the sample present in the needle should rapidly be heated immediately after the needle is inserted into a gas chromatograph through the sample-injection port thereof and accordingly, the needle preferably has an inner diameter ranging from 0.2 to 0.6 mm, preferably about 0.5 mm; an outer diameter ranging from 0.5 to 0.8 mm, preferably about 0.7 mm; and a length ranging from 3 to 10 cm, preferably on the order of 5 to 9 cm. The wall thickness of the needle is preferably thin from the viewpoint of heat conduction and the wall thickness thereof thus desirably falls within the range of from about 0.10 to 0.15 mm.

The method for fixing the adsorbent or concentrating medium within the needle is not likewise limited to any particular one, but it is sufficient to fill and seal the both ends of the needle (more specifically, the both ends of the adsorbent or concentrating medium), which has been packed with the adsorbent or concentrating medium, with, for instance, silica wool, stainless steel fiber nonwoven fabric, heat-resistant fibers such as Zylon (registered trademark) fibers and Kevlar (registered trademark) fibers.

When using the copolymer as an adsorbent or a concentrating medium, it may be used as a packing material for the loop of an injector for chromatograph.

Such a loop is desirably one produced from a metal such as stainless steel. The dimension thereof is not restricted to any particular one, but it preferably has an inner diameter ranging from about 0.3 to about 10 mm, preferably about 0.5 to about 1.0 mm; an outer diameter ranging from about 0.5 to about 12 mm, preferably about 1.6 to about 3.2 mm; and a length ranging from about 1.0 to about 100 cm, preferably about 2 to about 10 cm, from the viewpoint of the pressure resistance and inner volume of the loop. The wall thickness of the loop is preferably thin from the viewpoint of heat conduction and the wall thickness thereof thus desirably falls within the range of from about 0.5 to about 1.0 mm.

The kit for the preparation of a sample to be analyzed according to the present invention comprises a needle for SPME, which is packed with the foregoing adsorbent or concentrating medium; a syringe having a large volume (or a large volume syringe); and a syringe having a small volume (or a small volume syringe). The needle for SPME is fitted to the tip of the large volume syringe, followed by the aspiration of a large amount of a liquid or gaseous sample to thus adsorb an analyte present in the sample on the adsorbent or concentrating medium or concentrate the former in the latter. At this stage, a vacuum pump may be used for the aspiration. Similarly, the volumes of the large and small volume syringes are not restricted to specific ones, but the volumes are conveniently on the order of about 10 to about 500 ml and about 1 to about 5 ml, respectively for portable use.

Then the analyte present in the sample is adsorbed on the adsorbent or concentrating medium packed in the needle for SPME, the small volume syringe is substituted for the large volume syringe, the needle for SPME is inserted into a chromatograph through the sample-injection port thereof, an eluting solution charged in the small volume syringe is passed through the needle to thus elute the analyte adsorbed on the adsorbent or concentrating medium, the resulting eluate is injected into the chromatograph through the sample-injection port thereof to thus carry out the chromatography analysis.

Examples of chromatography techniques usable herein are gas chromatography and liquid chromatography.

EXAMPLES

The present invention will hereunder be described in more detail with reference to the following working Examples and Test Examples, but the present invention is not restricted to these specific Examples at all.

Example 1

Synthesis of Copolymer 1

To a 500 ml volume beaker, there was added 500 ml of water and then 15 g of polyvinyl alcohol (average molecular weight: about 22,000) was added to the beaker while stirring with a stirrer. The resulting mixture was heated after sufficient stirring and the polyvinyl alcohol was completely dissolved in water at an instance when the temperature of the system was raised up to about 50° C. After the complete dissolution of the polyvinyl alcohol, 15 g of sodium chloride was added to the resulting solution in small portions while maintaining the temperature of the solution at 50° C. After the sodium chloride was completely dissolved in the solution, a reaction solution containing 2.58 g of methacrylic acid, 29.70 g of ethylene glycol dimethacrylate, 0.26 g of azoisobutyronitrile and 12.9 g of di-n-butyl phthalate was dropwise added to the foregoing polyvinyl alcohol solution over about 5 minutes while sufficiently stirring the system by increasing the number of revolution of the stirrer. After the dropwise addition of the reaction solution, the temperature of the resulting solution was raised up to 85° C. at a rate of about 1° C./min and the reaction system was allowed to stand at that temperature for one hour to thus complete the reaction.

The revolution of the stirrer and the heating were stopped, the reaction system was allowed to stand for a period of time to precipitate the resulting polymer, the supernatant was discarded and hot water was added to the residue with stirring. These operations were repeated 4 to 5 times, the precipitates were likewise washed several times with acetone, then several times with ion-exchanged water maintained at room temperature, finally again several times with acetone, followed by the transfer of the copolymer to an evaporating dish, air-drying of the same at room temperature till the precipitates were not humid and further drying the same with heating in a dryer till any smell of acetone was completely eliminated.

Thus, 20 g of an intended copolymer was prepared. The resulting copolymer was in the form of beads each having a diameter ranging from 30 to 100 μm and the fine pore volume thereof was found to be 0.4 ml/g.

Example 2

Synthesis of Copolymer 2

The same procedures used in Example 1 were repeated except that the reaction solution used herein comprised 2.58 g of methacrylic acid, 29.70 g of ethylene glycol dimethacrylate, 0.52 g of azoisobutyronitrile and 32.28 g of di-n-butyl phthalate to obtain a copolymer.

Thus, 25 g of an intended copolymer was prepared. The resulting copolymer was in the form of beads each having a diameter ranging from 20 to 100 μm and the fine pore volume thereof was found to be 1 ml/g.

Example 3

Preparation of Needle 1

Figure 1:
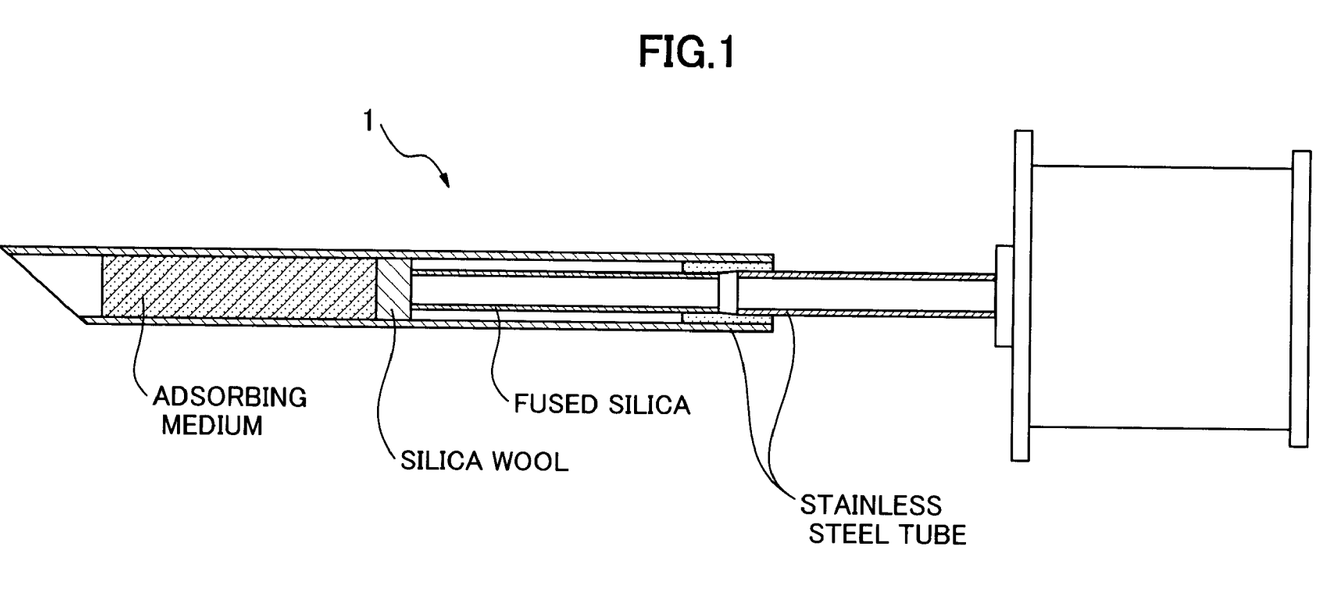
FIG. 1 is a cross sectional view showing the outline of a needle 1.

A needle as shown in FIG. 1 (a stainless steel tube having an outer diameter of 0.81 mm, an inner diameter of 0.51 mm and a length of 85 mm) was packed with the copolymer 1 prepared in Example 1 up to a height of 5 cm from the tip of the needle and then the needle packed with the copolymer was aged at 200° C. for 16 hours to thus give a needle 1 for SPME.

Example 4

Preparation of Needle 2

A needle as shown in FIG. 1 (a stainless steel tube having an outer diameter of 0.81 mm, an inner diameter of 0.51 mm and a length of 85 mm) was packed with the copolymer 1 prepared in Example 1 up to a height of 3 cm from the tip of the needle and then the needle packed with the copolymer was aged at 150° C. for 16 hours to thus give a needle 2 for SPME.

Example 5

Preparation of Needle 3

Figure 2:
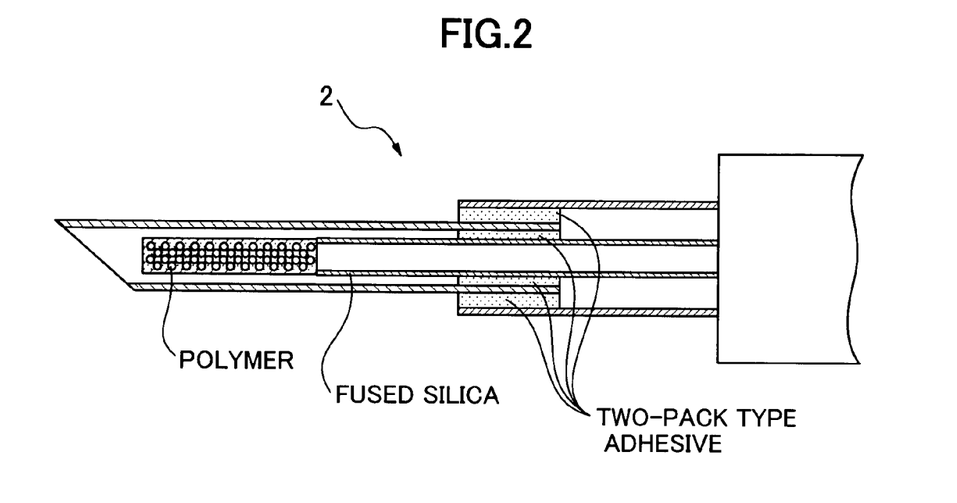
FIG. 2 is a cross sectional view showing the outline of a needle 2.

A needle as shown in FIG. 2 (a stainless steel tube having an outer diameter of 0.50 mm, an inner diameter of 0.30 mm and a length of 85 mm) was packed with the copolymer 1 prepared in Example 1 up to a height of 3 cm from the tip of the needle and then the needle packed with the copolymer was aged at 150° C. for 16 hours to thus give a needle 3 for SPME. Then the tip of the needle was calked in order to prevent any leakage of the copolymer through the tip of the needle, while the rear edge of the copolymer layer was sealed with a fused silica column having an outer diameter of 0.2 mm.

Example 6

Preparation of Needle 4

A needle as shown in FIG. 1 (a stainless steel tube having an outer diameter of 0.81 mm, an inner diameter of 0.51 mm and a length of 85 mm) was packed with the copolymer 2 prepared in Example 2 up to a height of 3 cm from the tip of the needle and then the needle packed with the copolymer was aged at 150° C. for 16 hours to thus give a needle 4 for SPME.

Example 7

Preparation of Needle 5

The outer side of a needle as shown in FIG. 1 (a stainless steel tube having an outer diameter of 0.81 mm, an inner diameter of 0.51 mm and a length of 85 mm) was ground or scraped away with a sand paper to an outer diameter of about 0.7 mm, packed with the copolymer 2 prepared in Example 2 up to a height of 3 cm from the tip of the needle and then the needle packed with the copolymer was aged at 150° C. for 15 hours to thus give a needle 5 for SPME.

Example 8

Preparation of Needle 6

A needle as shown in FIG. 6 (a stainless steel needle having an outer diameter of 0.7 mm, an inner diameter of 0.5 mm and a length of 85 mm) was packed with the copolymer 2 prepared in Example 2 up to a height of 3 cm from the tip of the needle. The copolymer was fixed by forcing Zylon fibers into the needle at the both ends of the copolymer. The needle packed with the copolymer was aged at 150° C. for 15 hours to thus give a needle 6 for SPME.

Test Examples 1 to 3

Test for Absorption-Desorption of Organic Solvent (i) A standard gas (1.0 ml) contained in a Tedlar (registered trademark) Bag was injected into a gas chromatograph (GC) to thus determine the peak areas for hexane, ethanol and toluene.
(ii) A needle packed with a copolymer was fitted to a syringe (1 ml) and a blank test was carried out by injecting 0.5 ml of air into the GC device to thus confirm that any peak was not detected at all.
(iii) The syringe of the needle was replaced by one having a volume of 20 ml and 4.5 ml of the gas contained in the Tedlar (registered trademark) Bag was sucked in over about 2 minutes. The syringe was immediately replaced by one having a volume of 1 ml, while the needle was not replaced and 0.5 ml of the gas in the Tedlar (registered trademark) Bag was likewise sucked in. The needle was immediately replaced by another needle free of any copolymer and the gas was injected into the GC device to thus confirm that there was not any solvent, which could pass through the needle without being adsorbed on the copolymer.
(iv) The needle packed with the copolymer containing the gaseous organic solvents adsorbed thereon was fitted to a 1 ml volume syringe and 0.5 ml of air was injected into the GC device to thus determine the peak area observed for each solvent component desorbed. In this respect, the air was injected into the GC device after the needle was inserted into the device through the gas-injection port thereof and then it was maintained under such conditions for 3 seconds. The rate of desorption was determined by comparing the resulting peak area with that obtained in the foregoing step (i).

Test Example 4

Test for Absorption-Desorption of Organic Solvent (i) A standard gas (1.0 ml) contained in a Tedlar (registered trademark) Bag was injected into a GC device to thus determine the peak areas for hexane, ethanol and toluene.
(ii) A needle 4 packed with a copolymer was fitted to a 1 ml volume syringe and a blank test was carried out by injecting 0.5 ml of air into the GC device to thus confirm that any peak was not detected at all.
(iii) The syringe of the needle 4 was replaced by a gas tight one having a volume of 10 ml, 10 ml of the gas contained in the Tedlar (registered trademark) Bag was sucked in twice over about 3 minutes and then 4.5 ml thereof was sucked in once (25 ml of the gas in total). The syringe was immediately replaced by one having a volume of 1 ml, while the needle 4 was not replaced and 0.5 ml of the gas in the Tedlar (registered trademark) Bag was likewise sucked in. The needle was immediately replaced by another needle free of any copolymer and the gas was injected into the GC device to thus confirm that there was not any solvent, which could pass through the needle without being adsorbed on the copolymer.
(iv) The needle 4 packed with the copolymer containing the gaseous organic solvents adsorbed thereon was fitted to a 1 ml volume syringe and 0.5 ml of air was injected into the GC device to thus determine the peak area observed for each solvent component desorbed. In this respect, the air was injected into the GC device after the needle 4 was inserted into the device through the gas-injection port thereof and then it was maintained under such conditions for 3 seconds. The rate of desorption was determined by comparing the resulting peak area with that obtained in the foregoing step (i).

Table 1 shows the results obtained in Test Examples 1 to 4 carried out using a variety of needles.

TABLE 1

| Test Ex. No. | Needle | Copolymer | Rate of Desorption (%) | | |
| --- | --- | --- | --- | --- | --- |
| | | | Hexane | Ethanol | Toluene |
| 1 | 1 | 1 | 70 | — | 64 |
| 2 | 2 | 1 | 80 | 85 | 69 |
| 3 | 3 | 1 | 95 | 100 | 86 |
| 4 | 4 | 2 | 92 | 100 | 88 |

Test Example 5

Test for Absorption-Desorption of Organic Solvent (i) There were injected, into a 500 ml volume Tedlar (registered trademark) Bag filled with nitrogen gas, 1 µl each of hexane, ethanol, ethyl acetate, methyl ethyl ketone and toluene as well as 3 µl of chloroform, these organic substances were vaporized in the bag, 5.0 ml of the resulting gas was injected into another 500 ml volume Tedlar (registered trademark) Bag filled with nitrogen gas and the product thus formed was used in this test as a standard gas. Then the standard gas (1.0 ml) in the Tedlar (registered trademark) Bag was injected into a GC device to thus determine the peak areas observed for hexane, ethanol, ethyl acetate, methyl ethyl ketone, toluene and chloroform.

(ii) A needle 4 packed with a copolymer was fitted to a 1 ml volume syringe and a blank test was carried out by injecting 0.5 ml of air into the GC device to thus confirm that any peak was not detected at all.

(iii) The syringe of the needle was replaced by a gas tight one having a volume of 10 ml, 10 ml of the gas contained in the Tedlar (registered trademark) Bag was sucked in twice over about 3 minutes and then 4.5 ml thereof was sucked in once (25 ml of the gas in total). The syringe was immediately replaced by one having a volume of 1 ml, while the needle 4 was not replaced and 0.5 ml of the gas in the Tedlar (registered trademark) Bag was likewise sucked in. The needle was immediately replaced by another needle free of any copolymer and the gas was injected into the GC device to thus confirm that there was not any solvent, which could pass through the needle without being adsorbed on the copolymer.

(iv) The needle packed with the copolymer containing the gaseous organic solvents adsorbed thereon was fitted to a 1 ml volume syringe and 0.5 ml of air was injected into the GC device to thus determine the peak area observed for each solvent component desorbed. In this respect, the air was injected into the GC device after the needle 4 was inserted into the device through the gas-injection port thereof and then it was maintained under such conditions for 3 seconds. The rate of desorption was determined by comparing the resulting peak area with that obtained in the foregoing step (i).

All of the rates of desorption observed for hexane, ethanol, ethyl acetate, methyl ethyl ketone, toluene and chloroform were found to be 100%.

Test Example 6

Test for Absorption-Desorption of Organic Solvent (i) There were injected, into a first 500 ml volume Tedlar (registered trademark) Bag filled with nitrogen gas, 1 µl each of hexane, ethanol, ethyl acetate, methyl ethyl ketone and toluene as well as 3 µl of chloroform, these organic substances were vaporized in the bag, 5.0 ml of the resulting gas was injected into a second 500 ml volume Tedlar (registered trademark) Bag filled with nitrogen gas and the product thus formed was used in this test as a standard gas. Then the standard gas (1.0 ml) in the second Tedlar (registered trademark) Bag was injected into a GC device to thus determine the peak areas observed for hexane, ethanol, ethyl acetate, methyl ethyl ketone, toluene and chloroform.

To the second Tedlar (registered trademark) Bag, there was injected 10 µl (the amount required for the saturation of the bag at 20° C.) of water using a micro syringe, 1 µl of the resulting gas was likewise injected into the GC device after confirming the complete evaporation of the water drop added and the peak areas observed for the foregoing solvents were determined to thus confirm that the results thus obtained were almost identical to those observed for the dry standard gas. If the water is not completely vaporized, a part of the ethanol is absorbed with the water in its liquid state and therefore, the concentration of ethanol in the gas phase is reduced and this in turn leads to the reduction of the peak area observed for ethanol.

(ii) A needle 4 packed with a copolymer was fitted to a 1 ml volume syringe and a blank test was carried out by injecting 1.0 ml of air into the GC device to thus confirm that any peak was not detected at all.

(iii) The syringe of the needle 4 was replaced by a gas tight one having a volume of 10 ml and 24.5 ml of the gas contained in the Tedlar (registered trademark) Bag was sucked in. The syringe was immediately replaced by one having a volume of 1 ml, while the needle was not replaced and 0.5 ml of the gas in the Tedlar (registered trademark) Bag was likewise sucked in. The needle was immediately replaced by another needle free of any copolymer and the gas was injected into the GC device to thus confirm that there was not any solvent, which could pass through the needle without being adsorbed on the copolymer.

(iv) The needle 4 packed with the copolymer containing the gaseous organic solvents adsorbed thereon was fitted to a 1 ml volume syringe and 0.5 ml of air was injected into the GC device to thus determine the peak area observed for each solvent component desorbed. In this respect, the air was injected into the GC device after the needle was inserted into the device through the gas-injection port thereof and then it was maintained under such conditions for 3 seconds. The rate of desorption was determined by comparing the resulting peak area with that obtained in the foregoing step (i).

The rates of solvent desorption were found to be 64%, 91%, 99%, 99%, 98% and 88% for hexane, ethanol, ethyl acetate, methyl ethyl ketone, toluene and chloroform, respectively.

The foregoing results indicate that if the copolymer absorbs moisture, the solvent desorption may be inhibited.

Test Example 7

Test for Absorption-Desorption of Organic Solvent

The same procedures used in Test Example 6 were repeated except for using the needle 5 in place of the needle 4 used in Test Example 6.

All of the rates of desorption observed for hexane, ethanol, ethyl acetate (EA), methyl ethyl ketone (MEK), toluene and chloroform were found to be 100%.

The foregoing results indicate that if the heat conductivity of the needle is improved by the reduction of the wall thickness of the needle, any reduction of the rates of desorption of, in particular, hexane, ethanol and chloroform can be inhibited.

Test Examples 8 to 15

Tests for Absorption-Desorption of Organic Solvents

The same procedures used in Test Example 7 were repeated except that a variety of existing packing materials were substituted for the copolymer packed in the needle 5. The results thus obtained are listed in the following Table 2 together with the results obtained in Test Example 7.

TABLE 2

| Test Ex. | Packing Material | Rate of Desorption (%) | | | | | |
|---|---|---|---|---|---|---|---|
| | | Hexane | EtOH | EA | MEK | CHCl$_3$ | Toluene |
| 7 | Copolymer 2 | 100 | 100 | 100 | 100 | 100 | 100 |
| 8 | Sunpak-A 100 pass | 81 | 10 | 81 | 77 | 59 | 85 |
| 9 | Porapak-Q 100/200 | 91 | 4 | 87 | 67 | 50 | 92 |
| 10 | Porapak-N 100/120 | 97 | 48 | 100 | 100 | 91 | 93 |
| 11 | TENAXTA-80/100 | 23 | 3 | 61 | 44 | 30 | 100 |
| 12 | Chromosrb 101 100/120 | 23 | 5 | 63 | 51 | 41 | 96 |
| 13 | Silica rod | 20 | 3 | 24 | 18 | 13 | 37 |
| 14 | Activated carbon | 63 | 57 | 43 | 41 | 51 | 28 |
| 15 | Silica gel 80/100 | 63 | 57 | 43 | 41 | 51 | 28 |

EtOH: ethanol;
EA: ethyl acetate;
MEK: methylethyl ketone.

Example 9

Preparation of Exchange Needle for SPME

Figure 4:
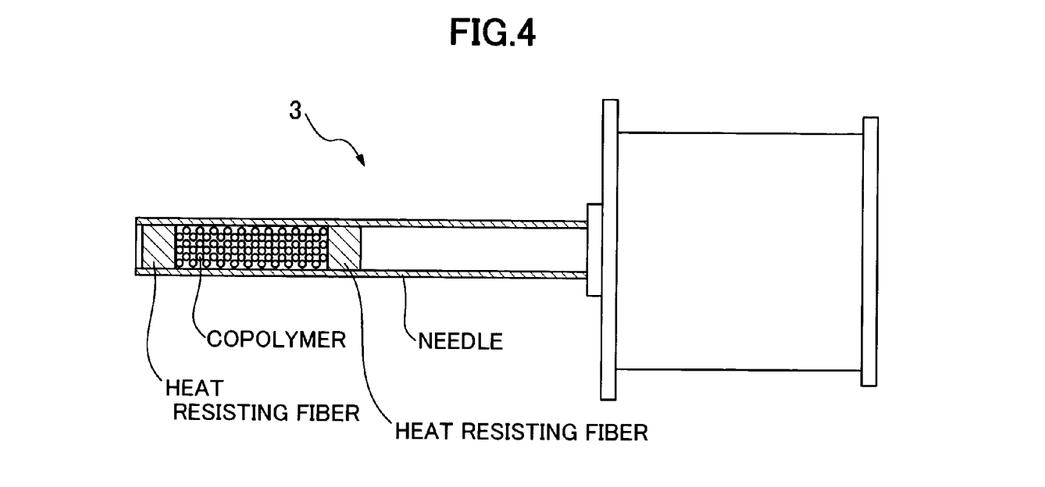
FIG. 4 is a cross sectional view showing the outline of a needle 3.
Figure 5:
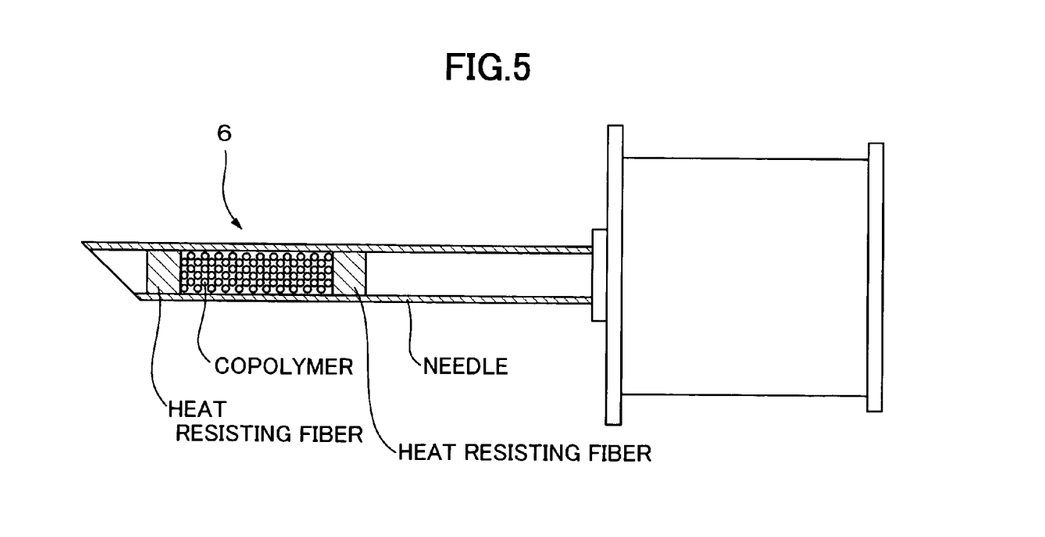
FIG. 5 is a cross sectional view showing the outline of a needle 6.

An exchange needle for liquid chromatography as shown in FIG. 4 (a stainless steel tube having an outer diameter of 0.7 mm, an inner diameter of 0.5 mm and a length of 52 mm) was packed with the copolymer 2 prepared in Example 2 up to a height of 2 cm from the tip of the exchange needle. The copolymer was fixed by forcing Zylon fibers into the needle at the both ends of the copolymer. The exchange needle was washed by passing 0.1 mL of methanol 5 times to thus form an exchange needle for SPME.

Example 10 & Preparation of Loop

Figure 3:
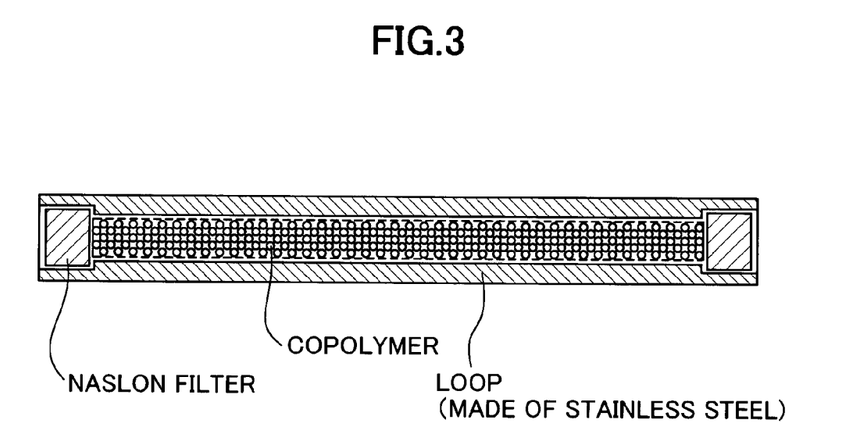
FIG. 3 is a cross sectional view schematically showing a loop packed with a copolymer.

A loop of an injector for liquid chromatography as shown in FIG. 3 (a stainless steel loop having an outer diameter of 1.6 mm, an inner diameter of 0.8 mm, a length of 100 mm and an inner volume of 50 μL) was packed with the copolymer 2 (33 μL) prepared in Example 2 and the copolymer was fixed by forcing Naslon filters (filters each prepared by sintering stainless steel fibers at a high temperature under a vacuum having a diameter of 0.85 mm and a thickness of 0.4 mm, available from Nippon Seisen Co., Ltd.) into the loop at the both ends of the copolymer. The resulting loop was fitted to an injector and then the loop was washed by passing a mobile phase (comprising methanol (80%) and water (20%)) through the same to thus give a loop for SPME.

Test Example 16

Test for Absorption-Desorption of Toluene, Naphthalene and Diphenyl

A: There was prepared a standard solution containing 780 ng/μL of toluene, 120 ng/μL of naphthalene and 20 ng/μL of diphenyl in methanol and 1 μL each of the solution was injected into a liquid chromatograph equipped with a usual sample loop (the loop prepared in Example 10, free of any copolymer packed therein) three times to determine the average peak areas for toluene, naphthalene and diphenyl, respectively.

B: A sample (1000 μL) prepared by diluting the foregoing standard sample 1000 times with water was injected into a liquid chromatograph equipped with the sample loop packed with the copolymer of the present invention and prepared in Example 10 three times to thus determine the average peak areas for toluene, naphthalene and diphenyl, respectively.

The results thus obtained are summarized in the following Table 3.

TABLE 3

| Component | A: Using the usual loop | B: Using the loop of the Invention | Peak Area Ratio: B/A |
|---|---|---|---|
| Toluene | 301694 | 234153 | 78% |
| Naphthalene | 398845 | 608900 | 153% |
| Diphenyl | 481623 | 652662 | 136% |

If the desorption is complete, the peak areas observed for the cases A and B are identical to one another since the same amount of each component is injected into the chromatograph. However, the peak areas observed when using a liquid chromatograph equipped with the sample loop comprising the copolymer of the present invention packed therein is sometimes higher than that observed for the usual loop and the former is sometimes smaller than the latter. Nevertheless, the foregoing results seem to indicate that the present invention would be a quite effective means for the concentration of a dilute sample (diluted 1000 times).

Test Example 17

Test for Absorption-Desorption of Toluene, Naphthalene and Diphenyl

A: The standard sample was injected into a liquid chromatograph three times (1 μL each) according to the procedures similar to those used in Test Example 16 to thus determine the average peak areas for toluene, naphthalene and diphenyl.
B: Subsequently, 1000 μL of a sample prepared by diluting the foregoing standard solution 1000 times with water was passed through the needle of Example 9, which had been packed with the copolymer of the present invention, 30 μL of methanol was passed through the needle to desorb the components adsorbed thereon and to thus inject the desorbed components into the liquid chromatograph. These desorbing operations were repeated five times to determine the sum of the resulting peak areas.

Further, the peak area ratios: B/A were likewise determined. The results thus obtained are summarized in the following Table 4.

TABLE 4

| Component | A | B | Peak Area Ratio: B/A |
|---|---|---|---|
| Toluene | 41053 | 81995 | 200% |
| Naphthalene | 54499 | 31547 | 58% |
| Diphenyl | 57871 | 27032 | 47% |

If the desorption is complete, the peak areas observed for the cases A and B are identical to one another, but the peak areas observed when using a liquid chromatograph equipped with the needle packed with the copolymer of the present invention is sometimes higher than that observed for the usual needle and the former is sometimes smaller than the latter. Nevertheless, the foregoing results seem to indicate that the needle of the present invention would be a quite effective means for the concentration of a dilute sample (diluted 1000 times).

Test Example 18

Test for Concentration of Solvent Gas Using Needle for SPME Used in GC Device

Desorption-adsorption tests were conducted using the needle 5 (packed with the copolymer 2) prepared in Example 7 and a standard gas of dried nitrogen gas balance.
A: There were determined the peak areas of the components present in 1 mL of the dried standard gas (the same as that used in Test Example 6).
B: After the aspiration of 25 mL of the foregoing standard gas, the desorption test was repeated 5 times to determine the sum of the peak areas.

The peak area ratio: B/A/25 thus determined are listed in the following Table 5 and the rates of desorption observed in each test are summarized in the following Table 6.

TABLE 5

| Component | A | B | Peak Area Ratio: B/A/25 |
|---|---|---|---|
| Hexane | 13846 | 373299 | 108% |
| Ethanol | 8040 | 227616 | 113% |
| Ethyl acetate | 7402 | 206780 | 112% |
| Methyl ethyl ketone | 10028 | 279883 | 112% |
| Chloroform | 6720 | 173212 | 103% |
| Toluene | 18152 | 493592 | 109% |

TABLE 6

| Test No. | 1 | 2 | 3 | 4 | 5 |
|---|---|---|---|---|---|
| Hexane | 99.7 | 0.3 | 0.1 | 0.0 | 0.0 |
| Ethanol | 100.0 | 0.0 | 0.0 | 0.0 | 0.0 |
| Ethyl acetate | 99.9 | 0.1 | 0.0 | 0.0 | 0.0 |
| Methyl ethyl ketone | 99.9 | 0.1 | 0.0 | 0.0 | 0.0 |
| Chloroform | 99.6 | 0.4 | 0.0 | 0.0 | 0.0 |
| Toluene | 99.8 | 0.2 | 0.1 | 0.0 | 0.0 |

The data listed in Table 5 indicate that the solvent gas may almost quantitatively be concentrated by the use of the SPME needle for GC and the data listed in Table 6 indicate that the solvent gas may almost completely be desorbed by only one desorption operation.

As has been described above in detail, the copolymer of the present invention does not have any specificity to general organic solvents, can thus adsorb all of the organic solvents and shows almost no desorption-adsorption hysteresis and therefore, the copolymer is excellent in the desorption characteristics. The needle packed with the copolymer can prevent any deterioration of the desorption characteristics due to the presence of water when the heat conductivity thereof is improved by the reduction of, in particular, the wall thickness of the needle. Moreover, a sample may be concentrated through the use of a loop packed with the copolymer.

What is claimed is:
1. A needle for solid-phase microextraction of a sample to be analyzed,
   wherein the needle is packed with an adsorbent or concentrating medium comprising a copolymer of methacrylic acid and ethylene glycol dimethacrylate,
   wherein the molar ratio of methacrylic acid and ethylene glycol dimethacrylate in said copolymer ranges from 1:1 to 1:10;
   wherein the needle is a metal needle;
   wherein the needle has an inner diameter ranging from 0.2 to 0.6 mm; an outer diameter ranging from 0.5 to 0.8 mm; and a length ranging from 3 to 10 cm; and
   wherein the copolymer is in the form of beads each (1) having a particle size ranging from about 20 μm to about 100 μm, (2) having fine pores therein, and (3) having been prepared by copolymerizing methacrylic acid and ethylene glycol dimethacrylate in the absence of another monomer and in the presence of a dispersing agent.

2. A kit for the preparation of a sample to be analyzed comprising the needle of claim 1, a syringe having a larger volume and a syringe having a smaller volume.

3. The needle of claim 1, wherein the molar ratio of methacrylic acid and ethylene glycol dimethacrylate in the copolymer ranges from 1:4 to 1:6.

4. The needle of claim 1, wherein the needle is a stainless steel needle.

5. The kit of claim 2, wherein the syringe having a larger volume has a volume of about 10 to about 500 ml and the syringe having a smaller volume has a volume of about 1 to about 5 ml.

6. The needle of claim 1, wherein the copolymer is in the form of beads each having a particle size ranging from about 30 μm to about 100 μm.

7. The needle of claim 1, wherein the copolymer is prepared in the presence of a water-soluble metal salt, a dispersing agent, a polymerization initiator and a swelling agent in an aqueous medium and is washed to remove water-soluble metal salt, dispersing agent, polymerization initiator and swelling agent, and dried.

8. The needle of claim 1 wherein copolymer is prepared in an aqueous solution comprising a water-soluble alkali metal salt, 1.0 to 5.0% by mass of polyvinyl alcohol having a weight average molecular weight of about 22,000-88,000 or 1.0 to 3.0% by mass of polyvinyl pyrrolidone having a weight average molecular weight of about 40,000-360,000, 0.5 to 2.0% by mass of a polymerization initiator, and up to 200% by mass of a swelling agent at a temperature of from 50 to 100° C. for 10 minutes to 5 hours.

9. The needle of claim 1 wherein the needle has an inner diameter of about 0.5 mm; an outer diameter of about 0.7 mm; and a length ranging from 5 to 9 cm.

10. The kit of claim 2 wherein the needle has an inner diameter of about 0.5 mm; an outer diameter of about 0.7 mm; and a length ranging from 5 to 9 cm.

11. The needle of claim 3 wherein the needle has an inner diameter of about 0.5 mm; an outer diameter of about 0.7 mm; and a length ranging from 5 to 9 cm.

12. The needle of claim 4 wherein the needle has an inner diameter of about 0.5 mm; an outer diameter of about 0.7 mm; and a length ranging from 5 to 9 cm.

13. The kit of claim 5 wherein the needle has an inner diameter of about 0.5 mm; an outer diameter of about 0.7 mm; and a length ranging from 5 to 9 cm.

14. The needle of claim 6 wherein the needle has an inner diameter of about 0.5 mm; an outer diameter of about 0.7 mm; and a length ranging from 5 to 9 cm.

15. The needle of claim 7 wherein the needle has an inner diameter of about 0.5 mm; an outer diameter of about 0.7 mm; and a length ranging from 5 to 9 cm.

16. The needle of claim 8 wherein the needle has an inner diameter of about 0.5 mm; an outer diameter of about 0.7 mm; and a length ranging from 5 to 9 cm.

17. The needle of claim 1, wherein said copolymer is in the form of beads each having a fine pore volume of 0.4 to 1 ml/g.

18. The needle of claim 1 wherein the needle has a wall thickness within the range of from about 0.10 and 0.15 mm.

* * * * *